(12) United States Patent
Maas et al.

(10) Patent No.: US 6,486,359 B1
(45) Date of Patent: Nov. 26, 2002

(54) CATALYST COMPRISING A COMPLEX OF A METAL OF SUBGROUP VIII BASED ON A PHOSPHINITE LIGAND, AND A METHOD FOR HYDROFORMYLATION

(75) Inventors: Heiko Maas, Schifferstadt; Rocco Paciello, Bad Dürkheim; Michael Röper, Wachenheim; Jakob Fischer, Kirchdorf, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/719,353

(22) PCT Filed: Jun. 18, 1999

(86) PCT No.: PCT/EP99/04243
§ 371 (c)(1),
(2), (4) Date: Dec. 12, 2000

(87) PCT Pub. No.: WO99/65606
PCT Pub. Date: Dec. 23, 1999

(30) Foreign Application Priority Data

Jun. 18, 1998 (DE) .......................... 198 27 232

(51) Int. Cl.[7] .............................. C07C 45/50
(52) U.S. Cl. .................. 568/454; 502/163; 556/14; 556/18; 556/19; 558/338; 558/339; 558/340
(58) Field of Search .............. 502/163; 558/338; 558/339, 340; 568/454; 556/14, 18, 19

(56) References Cited

U.S. PATENT DOCUMENTS

| | | | |
|---|---|---|---|
| 3,766,237 A | 10/1973 | Chia et al. | 260/465 |
| 4,755,624 A | 7/1988 | Phillips et al. | 568/454 |
| 5,312,996 A | 5/1994 | Packett | 568/454 |
| 5,356,967 A | 10/1994 | Böhshar et al. | 524/117 |
| 5,512,695 A | 4/1996 | Kreutzer et al. | 558/338 |
| 5,523,453 A | 6/1996 | Breikss | 558/338 |
| 5,530,150 A | 6/1996 | Takaya et al. | 556/18 |
| 5,739,372 A | 4/1998 | Regnat et al. | 558/82 |

FOREIGN PATENT DOCUMENTS

| | | |
|---|---|---|
| CA | 2110100 | 5/1994 |
| WO | WO 92/00306 | 1/1992 |
| WO | WO 95/28228 | 10/1995 |
| WO | WO 95/29153 | 11/1995 |
| WO | WO 96/11182 | 4/1996 |
| WO | WO 96/22968 | 8/1996 |

OTHER PUBLICATIONS

Mathey, J. Chem. Soc., Chem. Comm., pp. 191–192 (1980).*
Casalnuovo et al. "Ligand Electronic Effects in Asymmetric Catalysis: Enhanced Enantioselectivity in the Asymmetric Hydrocyanation of Vinylarenes" J.Am. Chem. Soc. vol. 116 (1994) pp. 9869–9882.
Baker et al. "Chelating Diphosphite Complexes of Nickel (O) and Platinum (O): Their Remarkable Stability and Hydrocyanation Activity" J. Am. Chem. Soc. Chem. Commun. (1991) pp. 803–804.
Baker et al. "Chiral Aryl Diphosphites : a New Class of Ligands for Hydrocyanation Catalysts" J. Chem. Soc. Chem Commun. (1991) pp. 1292–1293.
Tolman et al. "Homogenous Nickel–Catalyzed Olefin Hydrocyanation" Advances in Catalysts vol. 33 (1985) pp. 1–46.
Tolman et al. "Catalytic Hydrocyanation of Olefins by Nickel (0) Phosphite Complexes–Effects Of Lewis Acids" Organometallics vol. 3 (1984)pp. 33–43.
"Applied Homogenous Catalysis with Organometallic Compounds" vol. 1 (1996) pp. 465–486.
Beller et al. "Progress in Hydroformylation and carbonylation" Journal of Molecular Catalysts vol. 104 (1995) pp. 17–85.

* cited by examiner

Primary Examiner—Michael L. Shippen
(74) Attorney, Agent, or Firm—Keil & Weinkauf

(57) ABSTRACT

The invention relates to a catalyst which comprises at least one complex of a metal of group VIII, which comprises at least one uni-, bi- or multidentate phosphinite ligand in which the phosphorus atom and the oxygen atom of the phosphinite group are part of a 5- to 8-membered heterocycle, and to processes for hydroformylation and hydrocyanation of compounds which contain at least one ethylenic double bond in the presence of a catalyst of this type.

10 Claims, No Drawings

CATALYST COMPRISING A COMPLEX OF A METAL OF SUBGROUP VIII BASED ON A PHOSPHINITE LIGAND, AND A METHOD FOR HYDROFORMYLATION

The present invention relates to a catalyst which comprises at least one complex of a metal of group VIII, which comprises at least one uni-, bi- or multidentate phosphinite ligand in which the phosphorus atom and the oxygen atom of the phosphinite group are part of a 5- to 8-membered heterocycle, and to processes for the hydroformylation and hydrocyanation of compounds which contain at least one ethylenically unsaturated double bond in the present of a catalyst of this type.

Hydroformylation or oxo synthesis is an important industrial process and is used to prepare aldehydes from olefins, carbon monoxide and hydrogen. These aldehydes may, where appropriate, be hydrogenated with hydrogen in the same operation to give the corresponding oxo alcohols. The reaction itself is highly exothermic and generally proceeds under elevated pressure and at elevated temperatures in the presence of catalysts. The catalysts employed are Co, Rh or Ru compounds or complexes which may be modified with amine- or phosphine-containing ligands to influence the activity and/or selectivity. Additional promoters have not to date achieved any importance in practice. The hydroformylation reaction results, because of the possibility of addition of Co to each of the two C atoms in a double bond, in the formation of mixtures of isomeric aldehydes. In addition, when internal olefins are used, isomerization of the double bond from an internal toward a terminal position may occur. In these isomeric mixtures, the n aldehyde is generally favored over the iso aldehyde but, because the n aldehydes have considerably greater industrial importance, one aim is to optimize the hydroformylation catalysts to achieve greater n selectivity.

A review of hydroformylation processes is given in Beller et al., Journal of Molecular Catalysis A, 104 (1995), pages 17–85. None of the references mentioned therein describes hydroformylation catalysts based on bi- or multidentate phosphinite ligands where the phosphinite group is part of a 5- to 8-membered heterocycle.

EP-A 0 599 284 describes cycloolefin polymer molding compositions which are stabilized with an organophosphorus compound against unwanted oxidative, thermal and photochemical damage. Stabilizers which can be employed in this case are, inter alia, phosphinites in which the phosphorus and the oxygen atom in the phosphinite group are part of a 6-membered heterocycle. DE-A 40 21 195 and WO 92/00306 describe a process for preparing these organophosphorus compounds by Grignard synthesis, and the use thereof for stabilizing plastics. Complex compounds of these organophosphorus compounds and their use as ligands in hydroformylation catalysts are not described.

Catalytic hydrocyanation to prepare nitriles from olefins likewise has great industrial importance. This generally involves reacting mono-, di- or polyolefins in the presence of suitable catalysts with hydrogen cyanide to give mono-, di- and polynitriles or mixtures thereof, which are of outstanding importance in particular as amine precursors, e.g. for preparing polyamides.

"Applied Homogeneous Catalysis with Organometalic Compounds", Volume 1, VCH Weinheim, pp. 465 et seq., gives a general description of heterogeneous and homogeneous catalysis for addition of hydrogen cyanide onto olefins. The catalysts used for this are in particular those based on phosphine, phosphite and phosphonite complexes of nickel and palladium.

The usual catalysts for the hydrocyanation are, in particular, the nickel(0) phosphite catalysts mentioned above.

C. A. Tolman et al. describe in Organometallics 1984, 3, pp. 33 et seq. the catalytic hydrocyanation of olefins in the presence of nickel(0) phosphite complexes paying special attention to the effects of Lewis acids on the addition of hydrogen cyanide.

Advances in Catalysis, Volume 33, 1985, Academic Press Inc., pp. 1 et seq., gives a review-like description of homogeneous nickel-catalyzed hydrocyanation of olefins. The catalysts employed are nickel(0) complexes with phosphine and phosphite ligands.

J. Chem. Soc., Chem. Commun., 1991, p. 1292, describes chiral aryl diphosphites as ligands for hydrocyanation catalysts. The phosphite group in these ligands is bonded by two of its oxygen atoms to the 3 and 3' positions of a 2,2'-binaphthyl unit, with which it thus forms a 7-membered heterocycle. It is additionally possible for two of these heterocycles likewise to be linked via a 2,2'-binaphthyl unit to a bidentate chelating ligand.

J. Chem. Soc., Chem. Commun., 1991, pp. 803 et seq., describes chelate diphosphite complexes of nickel(0) and platinum(0) analogous thereto, employing a 2,2'-biphenyl unit in place of a 2,2'-binaphthyl unit.

WO 95/28228 describes a process for the hydrocyanation of aliphatic monoolefins which may additionally have an unconjugated nitrile group or an unconjugated or conjugated ester group. The nickel(0) catalysts employed in this case likewise comprise bidentate phosphite ligands in which the phosphite groups are parts of aryl-fused heterocycles.

WO 95/29153 describes a process for the hydrocyanation of monoolefins employing catalysts based on zero-valent nickel and unidentate phosphite ligands. The phosphite group in these ligands is once again, together with two of its oxygen atoms, part of an aryl-fused 7-membered heterocycle. The third oxygen atom of the phosphite group carries a t-butyl-substituted phenyl radical which may have further substituents.

WO 96/11182 describes a process for the hydrocyanation of aliphatic, monoethylenically unsaturated compounds in which the ethylenic double bond is not conjugated with another unsaturated group or in which the ethylenic double bond is conjugated with an ester group. In this case, a nickel(0) catalyst based on a multidentate phosphite ligand is employed in the presence of a Lewis acid as promoter. The phosphite groups in these multidentate ligands are in turn constituents of aryl-fused heterocycles and may be linked together via aryl-fused groups.

WO 96/22968 describes a process for the hydrocyanation of diolefinic compounds and for the isomerization of the resulting unconjugated 2-alkyl-3-monoalkenonitriles by reacting an acyclic aliphatic diolefin with a source of hydrogen cyanide. The reaction in this case takes place in the liquid phase. The hydrocyanation catalysts employed are analogous to those described in WO 96/11182.

U.S. Pat. No. 5,512,695 has a disclosure content corresponding to that of WO 95/28228.

Apart from the hydrocyanation catalysts based on uni-, bi- and multidentate phosphite ligands described above, catalysts based on phosphinite ligands are also known. J. Am. Chem. Soc., 1994, 116, pp. 9869 et seq. and U.S. Pat. No. 5,484,902 describe catalysts for the enantioselective hydrocyanation of aromatic vinyl compounds based on a chiral, non-racemic, bidentate chelating phosphinite ligand. The ligand preferably employed in this case is a phenyl 2,3-bis-O-(3,5-bis(trifluoromethyl)phenyl)phosphino-4,6-O-benzylidene-β-D-glucopyranoside.

U.S. Pat. No. 5,523,453 describes a process for the hydrocyanation of monoolefins which may additionally have a cyano group in the presence of a Lewis acid as promoter and of a nickel(0) catalyst. These catalysts have ligands based on chelating phosphinites where two aryl-substituted phosphinite groups are linked together via their oxygen atom and an aryl-fused alkylene bridge.

None of the abovementioned references describes hydrocyanation catalysts based on phosphinite ligands in which the phosphinite group is part of a 5- to 8-membered heterocycle.

U.S. Pat. No. 3,766,237 describes a process for the hydrocyanation of ethylenically unsaturated compounds which may have other functional groups, e.g. nitriles, in the presence of a nickel catalyst. These nickel catalysts have four ligands of the general formula M(X,Y,Z) where X, Y and Z are, independently of one another, a radical R or OR, and R is selected from alkyl and aryl groups having up to 18 carbon atoms. However, only phosphines and phosphites are explicitly mentioned therein and employed in the examples of the hydrocyanation. On the other hand there is no disclosure of the possibility of employing phosphinites in which the phosphinite group is part of a heterocycle as ligands for nickel(0) hydrocyanation catalysts.

It is an object of the present invention to provide novel catalysts based on complexes of a metal of group VIII. They are preferably intended to be suitable for hydroformylation and/or hydrocyanation and to have good catalytic activity.

We have found that this object is achieved by catalysts based on complexes of a metal of group VIII which comprise at least one uni-, bi- or multidentate phosphinite ligand where the phosphinite group is part of a 5- to 8-membered heterocycle.

The present invention thus relates to a catalyst comprising at least one complex of a metal of group VIII with at least one uni-, bi- or multidentate phosphinite ligand of the general formula I

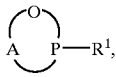
(I)

in which
A, together with the part of the phosphinite group to which it is bonded, is a 5- to 8-membered heterocycle which is optionally additionally fused once, twice or three times to cycloalkyl, aryl and/or hetaryl, where the fused groups may, independently of one another, each have one, two, three or four substituents selected from alkyl, alkoxy, halogen, nitro, cyano, carboxyl and carboxylate, $R^1$ is alkyl, aryl or hetaryl, each of which optionally has one, two or three substituents selected from alkyl, cycloalkyl, aryl, alkoxy, cycloalkyloxy, aryloxy, halogen, trifluoromethyl, nitro, cyano, carboxyl, carboxylate, acyl, sulfonyl, $NE^1E^2$ and alkylene-$NE^1E^2$, where $E^1$ and $E^2$ are identical or different and are selected from alkyl, cycloalkyl and aryl; or is a radical of the general formula II

 (II)

in which
X is either a $C_2$–$C_8$-alkylene bridge which is optionally interrupted by $SiR^aR^b$, N, $NR^c$, O or S, in which $R^a$ and $R^b$ are hydrogen, alkyl, alkoxy, halogen, trifluoromethyl, nitro or cyano, and $R^c$ is hydrogen, alkyl or aryl, where aryl is optionally mono- or disubstituted by alkyl, alkoxy, halogen, trifluoromethyl, nitro or cyano, optionally has one, two or three double bonds and/or is optionally fused once, twice or three times to aryl and/or hetaryl, where the aryl or hetaryl groups have, independently of one another, optionally one, two, three or four substituents selected from alkyl, cycloalkyl, aryl, alkoxy, cycloalkyloxy, aryloxy, halogen, trifluoromethyl, nitro, cyano, acyl, carboxyl, carboxylate, sulfonyl, sulfonate, $NE^1E^2$ and alkylene-$NE^1E^2$, where $E^1$ and $E^2$ have the meanings indicated previously, and adjacent fused rings are optionally connected by $SiR^aR^b$, N, $NR^c$, O or S or by a $C_1$–$C_6$-alkylene bridge which optionally additionally carries a group selected from $SiR^aR^b$, N, $NR^c$, O or S, in which $R^a$, $R^b$ and $R^c$ are as defined above; or an optionally substituted metallocene bridge; and
Y is a radical of the formula III

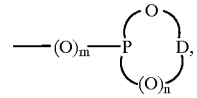
(III)

in which
D has the meanings indicated previously for A, and
m and n are, independently of one another, 0 or 1, or a salt thereof.

For the purpose of the present invention, the term "alkyl" comprises straight-chain and branched alkyl groups. These are preferably straight-chain or branched $C_1$–$C_8$-alkyl, preferably $C_1$–$C_6$-alkyl and particularly preferably $C_1$–$C_4$-alkyl groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl.

For the purpose of this invention, the term "alkylene" comprises straight-chain, optionally substituted alkylene groups with 1 to 8 carbon atoms. If X is an alkylene bridge, this has 2 to 8, preferably 3 to 6 and particularly preferably 3 to 5 carbon atoms. The alkylene bridge can be interrupted by hetero groups, e.g. Si, $SiR^aR^b$, N, $NR^c$, O or S, in particular O and $NR^c$, in which $R^a$ and $R^b$ are hydrogen, alkyl, alkoxy, halogen, trifluoromethyl, nitro or cyano, and $R^c$ is hydrogen, alkyl or aryl, where aryl is optionally mono- or disubstituted by alkyl, alkoxy, halogen, trifluoromethyl, nitro or cyano. Alkylene bridges having no heteroatoms are preferred for X. The alkylene bridge may moreover have one, two or three, preferably one or two, double bonds and/or may optionally be fused once, twice or three times, preferably once or twice, to aryl and/or hetaryl, preferably to aryl. Optionally fused aryl or hetaryl groups may have, independently of one another, one, two, three or four, preferably one, two or three, substituents selected from alkyl, cycloalkyl, aryl, alkoxy, cycloalkyloxy, aryloxy, halogen, trifluoromethyl, nitro, cyano, acyl, carboxyl, carboxylate, $NE^1E^2$ or alkylene-$NE^1E^2$, where $E^1$ and $E^2$ are identical or different and are selected from alkyl, cycloalkyl and aryl. If an alkylene group carries an $NE^1E^2$ group, it preferably has 1 to 4 carbon atoms and particularly preferably 1 or 2 carbon atoms, and methylene and ethylene are very particularly preferred. The substituents of the fused aryls and hetaryls are preferably selected from alkyl, alkoxy, trifluoromethyl, halogen and carboxylate.

The cycloalkyl group is preferably a $C_5$–$C_7$-cycloalkyl group such as cyclopentyl, cyclohexyl or cycloheptyl.

If the cycloalkyl group is substituted, it preferably has 1, 2, 3, 4 or 5, in particular 1, 2 or 3, substituents selected from alkyl, alkoxy or halogen.

Aryl is preferably phenyl, tolyl, xylyl, mesityl, naphthyl, anthryl, phenanthryl, naphthacenyl and, in particular, phenyl or naphthyl.

Substituted aryl radicals preferably have 1, 2, 3 or 4, in particular 1, 2 or 3, substituents selected from alkyl, alkoxy, carboxylate or halogen.

Hetaryl is preferably pyridyl, quinolinyl, acridinyl, pyridazinyl, pyrimidinyl or pyrazinyl.

Substituted hetaryl radicals preferably have 1, 2 or 3 substituents selected from alkyl, alkoxy or halogen.

The above statements about alkyl, cycloalkyl and aryl radicals apply correspondingly to alkoxy, cycloalkyloxy and aryloxy radicals.

The $NE^1E^2$ radicals are preferably N,N-dimethyl, N,N-diethyl, N,N-dipropyl, N,N-diisopropyl, N,N-di-n-butyl, N,N-di-tert-butyl, N,N-dicyclohexyl or N,N-diphenylamino.

Halogen is fluorine, chlorine, bromine and iodine, preferably fluorine, chlorine and bromine.

Carboxylate for the purpose of this invention is preferably a derivative of a carboxylic acid moiety, in particular a metal carboxylate, a carboxylic ester moiety or a carboxamide moiety, particularly preferably a carboxylic ester moiety.

If $R^1$ is a radical of the general formula II

    (II)

then X is preferably selected from 2,3-xylylene, 2,2'-biphenylylene, 2,2'-binaphthylylene, and arylene, in particular phenylene and naphthylene, linked by O, S and $NR^c$, where $R^c$ has the meaning indicated above. It is moreover possible for each phenyl unit additionally to have 1, 2 or 3 substituents, each naphthyl unit to have 1 to 4, preferably 1 to 3, substituents, selected from alkyl, cycloalkyl, aryl, alkyloxy, halogen, trifluoromethyl, nitro, cyano, acyl, carboxyl and carboxylate, in particular alkyl, alkoxy, trifluoromethyl and carboxylate. The phenyl and naphthyl units may additionally be linked by O, S or $NR^c$ or a $C_1$- to $C_6$-alkylene bridge, which may be interrupted by O, S or $NR^c$, where $R^c$ has the meaning already indicated above. Y is preferably a phosphite, phosphonite or phosphinite ligand where the O—P—O (n=1) or P—O group (n=0) is likewise part of a 5- to 8-membered heterocycle. The statements already made above about the heterocycle of the phosphinite ligand of the formula I according to the invention apply thereto. In particular, the meanings defined previously for A apply to D, and A and D can be identical or different.

X can, however, also be a metallocene bridge which optionally has one or more other substituents.

The term "metallocene" for the purpose of this invention is a sandwich metal complex with two $\eta^5$- or $\eta^6$-bonded unsaturated or aromatic ring systems which may be arranged parallel or at an angle, depending on the central metal atom. The metals suitable as central metal atom are all those which form stable sandwich complexes with adequate stability also under the conditions of use of the catalysts according to the invention, but especially Fe, Co, Ni, Ru, Os, Rh, Mn, Cr or V, particularly preferably Fe, Co and Ni. The metals in the metallocene complexes preferably have the formal oxidation numbers 0, +1 or +2. Suitable $\eta^5$- and $\eta^6$-complexable unsaturated or aromatic ring systems are cyclopentadienyl, indenyl, fluorenyl, azulenyl, benzene, naphthalene, anthracene and phenanthrene. Said ring systems may have, for example, 1 to 5, preferably 1 to 3, of the abovementioned substituents, in particular alkyl, alkoxy and alkylene-$NE^1E^2$ and, particularly preferably, methyl, isopropyl and tert-butyl.

X is preferably a radical of the formula IV.1, IV.2, IV.3, IV.4, IV.5, IV.6, IV.7 or IV.8

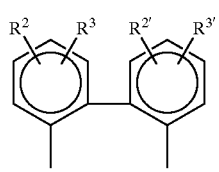    (IV.1)

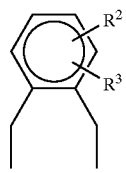    (IV.2)

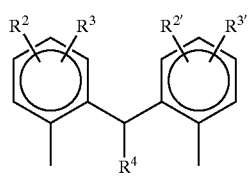    (IV.3)

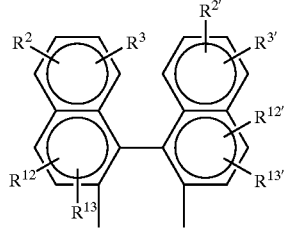    (IV.4)

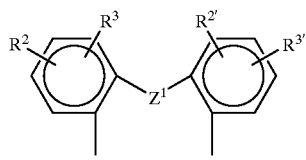    (IV.5)

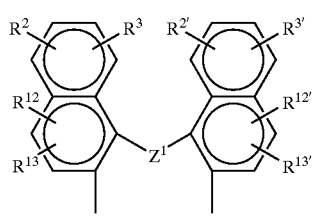    (IV.6)

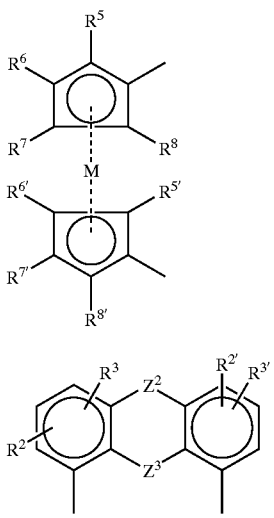

(IV.7)

(IV.8)

in which

R², R²', R³ and R³' are, independently of one another, hydrogen, alkyl, alkoxy, halogen, trifluoromethyl, nitro, cyano, acyl, carboxyl or carboxylate, R⁴ is hydrogen, alkyl, preferably methyl, or aryl, preferably phenyl, which may optionally be substituted by alkyl, alkoxy, halogen, trifluoromethyl, nitro or cyano, and R⁵, R⁵', R⁶, R⁶', R⁷, R⁷', R⁸, R⁸', R¹², R¹²', R¹³ and R¹³' meanings mentioned for R² and R³ or are, independently of one another, selected from cycloalkyl, aryl or alkyl, which may be interrupted by an oxygen atom or substituted by a radical of the formula NE¹E², where E¹ and E² have the meaning indicated above; or in each case two adjacent substituents R⁵, R⁶, R⁷, R⁸ and/or R⁵', R⁶', R⁷', R⁸' represent, with the part of the cyclopentadienyl ring connecting them, an aromatic or nonaromatic 5- to 7-membered carbocycle or heterocycle, where the heterocycle has 1, 2 or 3 heterogroups selected from O, N, NR$^c$ and S, M is Fe, Co, Ni, Ru, O, S Rh, Mn, Cr or V, Z¹ is O, S and NR$^c$ or a C₂- to C₃-alkylene bridge which is interrupted by O, S or NR$^c$, Z² and Z³ are, independently of one another, CH₂, SiR$^a$R$^b$, O, S, NR$^c$ or CR$^a$R$^b$, where R$^a$, R$^b$ and R$^c$ each have the meaning indicated above.

The above statements about preferred A radicals apply correspondingly to preferred D radicals.

When one of the radicals R⁵, R⁵', R⁶, R⁶', R⁷, R⁷', R⁸ or R⁸' in IV.7 is alkyl which is interrupted by an oxygen atom in ether linkage, they may be, for example, 2-methoxyethyl, 2-ethoxyethyl, 2-propoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-butoxybutyl.

When one of the radicals R⁵, R⁵', R⁶, R⁶', R⁷, R⁷', R⁸ or R⁸' in IV.7 is alkyl which is substituted by a radical of the formula NE¹E², they may be, for example, N,N-dimethylaminomethyl, N,N-dimethylaminoethyl, N,N-diethylaminomethyl, N,N-diethyl-aminoethyl or N,N-dimethylaminopropyl.

When in each case two of the substituents R⁵, R⁶, R⁷, R⁸ and/or R⁵', R⁶', R⁷', R⁸' in adjacent positions in IV.7 represent, together with the part of the cyclopentadienyl ring connecting them, an aromatic or nonaromatic 5- to 7-membered carbocycle or heterocycle which additionally has 1, 2 or 3 heteroatoms selected from O, N and S, they may be, for example, indenyl, fluorenyl, azulenyl, etc.

The two cyclopentadienyl rings in the metallocene of the formula IV.7 may be present in eclipsed or staggered conformation with varying conformational angles. The planes of the cyclopentadienyl rings may be parallel or inclined relative to one another, for example, depending on the central metal.

A preferred embodiment of the invention comprises catalysts which comprise at least one phosphinite ligand of the formula I, where A, together with the part of the phosphinite group to which it is bonded, is a 5- or 6-membered heterocycle which may optionally be fused once or twice to aryl and/or hetaryl, where the fused groups may have one, two or three of the substituents indicated previously.

The A radical is then, for example, a 2,2'-biphenylylene, 2,2'-binaphthylylene or 2,3-xylylene radical, which may have 1, 2 or 3 substituents selected from alkyl, alkoxy or halogen. Alkyl in this case is preferably C₁–C₄-alkyl and, in particular, t-butyl. Alkoxy in this case is preferably C₁–C₄-alkoxy and, in particular, methoxy. Halogen is, in particular, fluorine, chlorine or bromine. The above statements about preferred A radicals apply correspondingly to preferred D radicals.

In another preferred embodiment, the catalysts according to the invention comprise at least one phosphinite ligand of the formula I where R¹ is phenyl or naphthyl, which may have one, two or three of the following substituents: alkyl, alkoxy, halogen, nitro, cyano, carboxyl or NE¹E² where E¹ and E² have the meanings indicated previously, or a radical of the formula II in which X is a C₄–C₅-alkylene bridge which may have one or two double bonds and/or may be fused once or twice to aryl and/or hetaryl, where the aryl or hetaryl groups may have one, two or three of the following substituents: alkyl, cycloalkyl, aryl, alkoxy, cycloalkyloxy, aryloxy, halogen, nitro, cyano, carboxyl, carboxylate, alkylene-NE¹E² or NE¹E², where E¹ and E² have the meanings indicated previously, and Y is a radical of the formula III in which D is a radical of the formulae IV.1, IV.2, IV.3, IV.4, IV.5, IV.6 or IV.8.

If R¹ is phenyl or naphthyl, this preferably has 1, 2 or 3 substituents selected from C₁–C₄-alkyl, C₁–C₄-alkoxy or halogen. The substituents are particularly selected from t-butyl, methoxy, trifluoromethyl, fluorine, chlorine and bromine.

If R¹ is a radical of the formula II in which X is a C₄–C₅-alkylene bridge, the latter is preferably fused once or twice to phenyl and/or naphthyl, where the phenyl or naphthyl groups may have 1, 2 or 3 of the following substituents: t-butyl, ethoxy, carboxylate, fluorine, chlorine or bromine.

In a suitable embodiment, the phosphinite ligands of the formula I are selected from ligands of the formula Ia to Ii

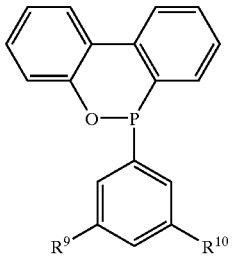

(Ia)

-continued (Ib)
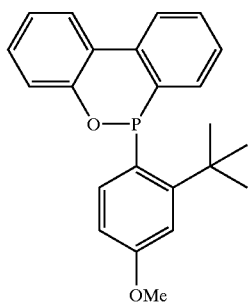

(Ic)
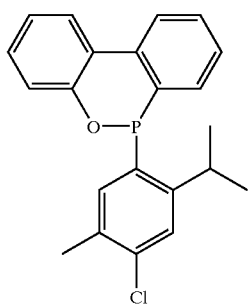

(Id)
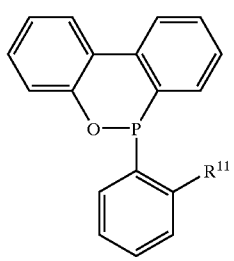

(Ie)
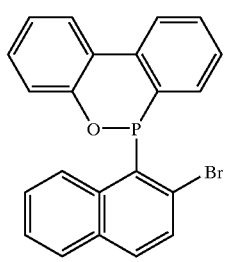

(If)
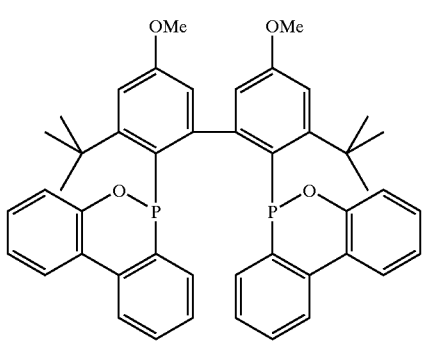

-continued (Ig)
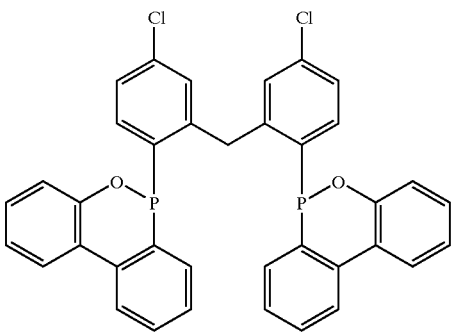

(Ih)
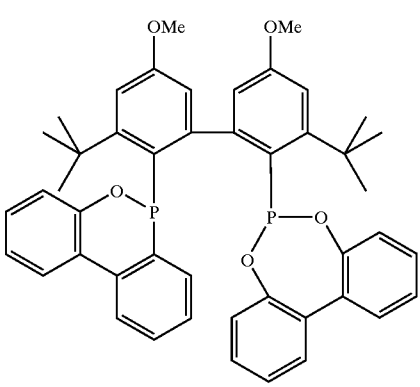

(Ii)
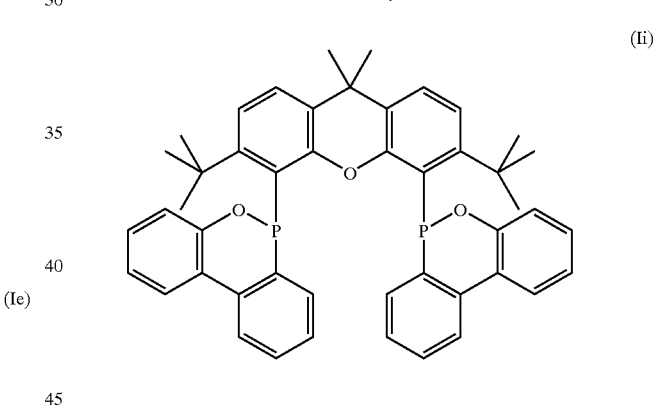

in which $R^9$ and $R^{10}$ are, independently of one another, hydrogen or trifluoromethyl, $R^{11}$ is fluorine or trifluoromethyl.

The catalysts according to the invention may have one or more of the phosphinite ligands of the formula I. In addition to the ligands of the general formula I described previously, they may also have at least one other ligand selected from halides, amines, carboxylates, acetylacetonate, aryl- or alkylsulfonates, hydride, CO, olefins, dienes, cycloolefins, nitrites, N-containing heterocycles, aromatic and heteroaromatic compounds, ethers, $PF_3$, and uni-, bi- and multidentate phosphine, phosphinite, phosphonite and phosphite ligands. These other ligands may likewise be uni-, bi- or multidentate and coordinate to the metal atom of the catalyst complex. Examples of other suitable phosphorus-containing ligands are the usual phosphine, phosphonite and phosphite ligands.

The phosphinite ligands of the formula I employed according to the invention can be prepared, for example, by reacting a hydroxyl-containing compound of the formula V with a phosphorus trihalide, preferably $PCl_3$, to give a compound of the formula VI. The latter is then reacted with an organometallic compound of the formula $R^1[M(Q)_q]_r$. The latter is prepared from $R^1[(Q)_q]_r$ and employed as the compound generated in situ or previously isolated. The preparation can be illustrated by the following scheme

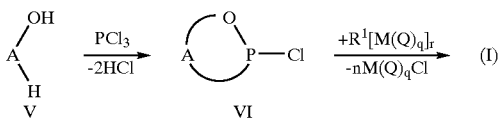

where A and $R^1$ have the meanings indicated previously, and M is lithium or magnesium, X is H, Cl, Br, q is 0 or 1 and r is 1 or 2.

A process of this type for synthesizing phosphinites is described in WO 92/00306, which is incorporated herein by reference.

Examples of suitable compounds of the formula V are 2-biphenylol, 2-binaphthylol, 4-phenyl-2-biphenylol, 3,3',5,5'-tetra-t-butyl-2-biphenylol, 3,3'-di-t-amyl-5,5'-dimethoxy-2-biphenylol, 3,3'-di-t-butyl-5,5'-dimethoxy-2-biphenylol, 3,3'-di-t-butyl-2-biphenylol, 3,3'-di-t-butyl-6,6'-dimethyl-2-biphenylol, 3,3',5,5'-tetra-t-butyl-6,6'-dimethyl-2-biphenylol, 3,3'-di-t-butyl-5,5'-di-t-butoxy-2-biphenylol, 3,3'-di-t-hexyl-5,5'-dimethoxy-2-biphenylol, 3-t-butyl-5,5'-dimethoxy-2-biphenylol, 1,1'-biphenyl-3,3'-di[2-(1,3-dioxacyclohexane)]-5,5'-dimethoxy-2-ol, 3,3'-diformyl-5,5'-dimethoxy-2-biphenylol and 1,1'-biphenanthryl-2-ol, in particular 2-biphenylol and 2-binaphthylol.

Examples of suitable compounds of the formula $R^1[(Q)_q]_r$ are unsubstituted aromatic compounds (Q=H) such as benzene, naphthalene, tetralin, anthracene or phenanthrene, especially benzene and naphthalene, monosubstituted aromatic compounds such as haloaromatics (Q=Cl, Br, I), for example halobenzene, halonaphthalene, especially chlorobenzene and bromobenzene, and monoalkyl- or monoarylaromatics, where alkyl or aryl may have the meaning already defined previously, but especially $C_1$–$C_8$-alkyl radicals or unsubstituted or substituted phenyl radicals. Examples of suitable monoalkylaromatics (Q=H) are toluene, ethylbenzene, n-propylbenzene, cumene, n-butylbenzene, sec-butylbenzene and tert-butylbenzene, especially toluene, cumene and tert-butylbenzene. Examples of suitable monoarylaromatics are biphenyl and substituted biphenyls.

Compounds of the formula $R^1[(Q)_q]_r$ which are likewise suitable are polysubstituted aromatic compounds such as alkyl- or aryl-substituted haloaromatics, polyalkyl- and/or polyaryl-substituted aromatic compounds and substituted or unsubstituted metallocenes. Examples of suitable alkyl-substituted haloaromatics (Q=Cl, Br, I) are 2-alkyl- or 4-alkyl-substituted haloaromatics, where alkyl may have the meaning already defined previously and is, in particular, $C_1$–$C_8$-alkyl and, particularly preferably, methyl, ethyl, isopropyl and tert-butyl. 2-Methylchlorobenzene, 2-methylbromobenzene, 4-methylchlorobenzene, 4-methylbromobenzene, 2-tert-butylchlorobenzene, 2-tert-butylbromobenzene, 4-tert-butylchlorobenzene and 4-tert-butylbromobenzene are particularly preferred.

Examples of suitable aryl-substituted haloaromatics (Q=Cl, Br, I) are 2-aryl- or 4-arylhaloaromatics, where aryl can have the meaning already defined previously and is, in particular, phenyl and substituted phenyl radicals and preferably phenyl, 2-tolyl, 4-tolyl and 2,4-dimethylphenyl. Biphenyl, 9,9-dimethylxanthene and 4,5-dibromo-2,7-di-tert-butyl-9,9-dimethylxanthene are particularly preferred.

The compounds of the formula I can if required be isolated and purified by known methods such as distillation, crystallization, chromatography and the like.

A preferred area of use of the catalysts according to the invention is for the hydroformylation of olefins.

In general under the hydroformylation conditions there is formation, from the catalysts or catalyst precursors employed in each case, of catalytically active species of the general formula $H_xM_y(CO)_zL_q$ in which M is a metal of group VIII, L is a phosphonite ligand according to the invention, and q, x, y and z are integers depending on the valency and nature of the metal and on the covalence of the ligand L. It is preferred for z and q independently of one another to have a value of at least 1, e.g. 1, 2 or 3. The total of z and q is preferably from 2 to 5. It is moreover possible for the complexes to have if required at least one of the other ligands described previously in addition.

The metal M is preferably cobalt, ruthenium, rhodium, palladium, platinum, osmium or iridium and, in particular cobalt, rhodium and ruthenium.

In a preferred embodiment, the hydroformylation catalysts are prepared in situ in the reactor employed for the hydroformylation reaction. If required, however, the catalysts according to the invention can also be prepared separately and isolated by conventional processes. To prepare the catalysts according to the invention in situ, at least one phosphinite ligand of the general formula I, a compound or a complex of a metal of group VIII, where appropriate at least one other additional ligand and, where appropriate, an activator are reacted in an inert solvent under the hydroformylation conditions.

Examples of suitable rhodium compounds or complexes are rhodium(II) and rhodium(III) salts such as rhodium(III) chloride, rhodium(III) nitrate, rhodium(III) sulfate, potassium rhodium sulfate, rhodium(II) or rhodium(III) carboxylate, rhodium(II) and rhodium(III) acetate, rhodium (III) oxide, salts of rhodium(III) acid, trisammonium hexachlororhodate(III) etc. Rhodium complexes are also suitable, such as rhodium biscarbonylacetylacetonate, acetylacetonatobisethylenerhodium(I) etc. Rhodium biscarbonylacetylacetonate or rhodium acetate are preferably employed.

Also suitable are ruthenium salts or compounds. Examples of suitable ruthenium salts are ruthenium(III) chloride, ruthenium(IV), ruthenium(VI) or ruthenium(VIII) oxide, alkali metal salts of ruthenium oxoacids, such as $K_2RuO_4$ or $KRuO_4$, or complex compounds of the general formula $RuX^1X^2L^1L^2(L^3)_n$, in which $L^1$, $L^2$, $L^3$ and n have the meanings indicated above and $X^1$, $X^2$ have the meanings indicated for X (see above), e.g. $RuHCl(CO)(PPh_3)_3$. It is also possible to use the ruthenium metal carbonyls such as triruthenium dodecacarbonyl or hexaruthenium octadecacarbonyl, or mixed forms in which CO is partly replaced by ligands of the formula $PR_3$, such as $Ru(CO)_3(PPh_3)_2$, in the process according to the invention.

Examples of suitable cobalt compounds are cobalt(II) chloride, cobalt(II) sulfate, cobalt(II) carbonate, cobalt(II) nitrate, their amine or hydrate complexes, cobalt carboxylates such as cobalt acetate, cobalt ethylhexanoate, cobalt naphthoate, and the cobalt-caprolactamate complex. In this case too it is possible to employ the carbonyl complexes of cobalt, such as dicobalt octacarbonyl, tetracobalt dodecacarbonyl and hexacobalt hexadecacarbonyl.

Said compounds of cobalt, rhodium and ruthenium are known in principle and are adequately described in the literature, or they can be prepared by the skilled worker in analogy to the compounds already known.

Examples of suitable activators are Brönsted acids, Lewis acids such as $BF_3$, $AlCl_3$, $ZnCl_2$ and Lewis bases.

The solvents preferably employed are the aldehydes which are produced on hydroformylation of the particular olefins, and the higher-boiling products of secondary reactions thereof, e.g. aldol condensation products. Other suitable solvents are aromatic compounds such as toluene, hydrocarbons or mixtures of hydrocarbons, also for diluting the abovementioned aldehydes and the aldehyde secondary products. Where the ligands are adequately hydrophilized, it is also possible to employ water, alcohols such as methanol, ethanol, n-propanol, isopropanol, n-butanol and isobutanol, ketones such as acetone and methyl ethyl ketone etc.

The ratio of the molar quantities of phosphinite ligand of the general formula I and of metal of group VIII is generally in the range from about 1:1 to 1000:1.

The invention further relates to a process for the hydroformylation of compounds which contain at least one ethylenic double bond by reaction with carbon monoxide and hydrogen in the presence of at least one of the hydroformylation catalysts according to the invention.

Suitable substrates for the hydroformylation process according to the invention are in principle all compounds which contain one or more ethylenic double bonds. These include, for example, olefins such as a-olefins, internal straight-chain and internal branched olefins. Examples of suitable a-olefins are ethylene, propene, 1-butene, 1-pentene, 1-hexene, 1-heptene, 1-octene, 1-nonene, 1-decene, 1-undecene, 1-dodecene etc.

Suitable straight-chain internal olefins are preferably $C_4$–$C_{20}$-olefins such as 2-butene, 2-pentene, 2-hexene, 3-hexene, 2-heptene, 3-heptene, 2-octene, 3-octene, 4-octene etc.

Suitable branched internal olefins are preferably $C_4$–$C_{20}$-olefins such as 2-methyl-2-butene, 2-methyl-2-pentene, 3-methyl-2-pentene, branched internal heptene mixtures, branched internal octene mixtures, branched internal nonene mixtures, branched internal decene mixtures, branched internal undecene mixtures, branched internal dodecene mixtures etc.

Suitable olefins for the hydroformylation are additionally $C_5$–$C_8$-cycloalkenes such as cyclopentene, cyclohexene, cycloheptene, cyclooctene and derivatives thereof, such as their $C_1$–$C_{20}$-alkyl derivatives with 1 to 5 alkyl substituents. Suitable olefins for the hydroformylation are additionally vinylaromatic compounds such as styrene, α-methylstyrene, 4-isobutylstyrene etc. Suitable olefins for the hydroformylation are additionally α,β-ethylenically unsaturated mono- and/or dicarboxylic acids, and their esters, monoesters and amides, such as acrylic acid, methacrylic acid, maleic acid, fumaric acid, crotonic acid, itaconic acid, methyl 3-pentenoate, methyl 4-pentenoate, methyl oleate, methyl acrylate, methyl methacrylate, unsaturated nitrites such as 3-pentenonitrile, 4-pentenonitrile, acrylonitrile, vinyl ethers such as vinyl methyl ether, vinyl ethyl ether, vinyl propyl ether etc., $C_1$–$C_{20}$-alkenols, -alkenediols and -alkadienols such as 2,7-octadien-1-ol. Suitable substrates are additional di- or polyenes with isolated or conjugated double bonds. These include, for example, 1,3-butadiene, 1,4-pentadiene, 1,5-hexadiene, 1,6-heptadiene, 1,7-octadiene, vinylcyclohexene, dicyclopentadiene, 1,5,9-cyclododecatriene, and butadiene homo- and copolymers.

The hydroformylation reaction can be carried out continuously, semicontinuously or batchwise.

Reactors suitable for the continuous reaction are known to the skilled worker and are described, for example, in Ullmanns Enzyklopädie der technischen Chemie, Volume 1, 3rd edition, 1951, pp. 743 et seq.

Suitable pressure-resistant reactors are likewise known to the skilled worker and are described, for example, in Ullmanns Enzyklopädie der technischen Chemie, Volume 1, 3rd edition, 1951, pp. 769 et seq. An autoclave will generally be used for the process according to the invention and can, if required, be provided with a stirrer and be lined.

The carbon monoxide and hydrogen synthesis gas employed in the process according to the invention may have a composition varying within wide limits. The molar ratio of carbon monoxide to hydrogen is usually about 5:95 to 70:30, preferably from 40:60 to 60:40. A molar ratio of carbon monoxide to hydrogen in the region of about 1:1 is particularly preferably employed.

The temperature in the hydroformylation reaction is generally in the range from about 20 to 180° C., preferably about 50 to 150° C. The reaction is ordinarily carried out at the partial pressure of the reaction gas at the chosen reaction temperature. The pressure is generally in the range from about 1 to 700 bar, preferably 1 to 600 bar, in particular 1 to 300 bar. The reaction pressure may be varied depending on the activity of the hydroformylation catalyst according to the invention which is employed. The catalysts according to the invention based on phosphinite ligands generally allow reaction in a lower-pressure region, such as in the range from 1 to 100 bar.

The hydroformylation catalysts according to the invention can be removed from the discharge from the hydroformylation reaction by conventional processes known to the skilled worker and can generally be employed anew for the hydroformylation.

The catalysts according to the invention advantageously show high activity so that the appropriate aldehydes are ordinarily obtained in good yields. In addition, on hydroformylation of α-olefins and of internal linear olefins, they show very low selectivity for the hydrogenation product of the olefin employed.

The hydroformylation process according to the invention is suitable and preferred for preparing a mixture of isomeric aldehydes, in which case the compound employed for the hydroformylation contains at least one terminal double bond, wherein a mixture of isomeric aldehydes which has an n/iso ratio of at least 3:1, in particular of 5:1, particularly preferably of 8:1, is obtained.

The present invention further relates to the mixture of isomeric aldehydes which has an n/iso ratio of 8:1 or greater and is obtainable by this process.

The catalysts according to the invention which have been described previously and comprise chiral phosphinite ligands of the formula I are suitable for enantioselective hydroformylation.

Another preferred area of use of the catalysts according to the invention is the hydrocyanation of olefins. The hydrocyanation catalysts according to the invention also comprise complexes of a metal of group VIII, in particular cobalt, nickel, ruthenium, rhodium, palladium, platinum, preferably nickel, palladium and platinum, and very particularly preferably nickel. The metal is ordinarily present with a valency of zero in the metal complex according to the invention. The metal complexes can be prepared as already described previously for the use as hydroformylation catalysts. The same applies to the in situ preparation of the hydrocyanation catalysts according to the invention.

Hydrocyanation catalysts according to the invention with nickel(0) as metal can be prepared by reacting at least one phosphinite ligand of the formula I with nickel or a nickel compound in the presence of a reducing agent or with a nickel complex in an inert solvent. Examples of suitable nickel compounds in this case are compounds in which the transition metal assumes an oxidation state of greater than zero, and which are reduced in situ in the reaction with the phosphinite ligand of the formula I, where appropriate in the presence of a suitable reducing agent. These include, for example, the halides, preferably the chlorides, and the acetates of the transition metals mentioned previously. $NiCl_2$ is preferably employed. Examples of suitable reducing agents are metals, preferably alkali metals, such as Na and K, aluminum, zinc and trialkylaluminum compounds.

If complex compounds of the transition metal are employed for preparing the phosphinite-nickel(0) complexes, the transition metal preferably already has a valency of zero in these compounds. The complexes preferably employed for the preparation have ligands which correspond to the additional ligands which have been mentioned previously in the complexes according to the invention. In this case, preparation takes place by partial or complete replacement of ligands by the phosphinite ligands of the formula I described previously.

In a suitable embodiment of the process according to the invention, the nickel complex is bis(1,5-cyclooctadiene)nickel(0).

Examples of suitable inert solvents for preparing the nickel(0) complexes are aromatic compounds such as benzene, toluene, ethylbenzene, chlorobenzene, ethers, preferably diethyl ether and tetrahydrofuran, or haloalkanes, for example dichloromethane, chloroform, dichloroethane and trichloroethane. The temperature for this is in the range from $-70°$ C. to $150°$ C., preferably from $0°$ C. to $100°$ C., particularly preferably at approximately room temperature.

If elemental nickel is employed to prepare the phosphinite-nickel(0) complexes, it is preferably in the form of a powder. The reaction of nickel and of phosphonite ligand preferably takes place in a product of the hydrocyanation reaction as solvent, e.g. in a mixture of monoolefinic $C_5$-mononitriles or, preferably, in 3-pentenenitrile. It is also possible where appropriate to employ the ligand as solvent. The temperature is in the range from about 0 to $150°$ C., preferably 60 to $100°$ C.

The hydrocyanation catalysts may, where appropriate, be prepared in situ in analogy to the process described for the hydroformylation catalysts.

The ratio of the molar quantities of phosphinite ligand of the general formula I and metal of group VIII is generally in the range from about 1:1 to 1000:1.

The invention further relates to a process for preparing nitrites by catalytic hydrocyanation, wherein the hydrocyanation takes place in the presence of at least one of the catalysts according to the invention described previously. Olefins suitable for the hydrocyanation are generally the olefins mentioned previously as starting materials for the hydroformylation. A specific embodiment of the process according to the invention relates to the preparation of mixtures of monoolefinic $C_5$-mononitriles with unconjugated C=C and C≡N bonds by catalytic hydrocyanation of 1,3-butadiene or 1,3-butadiene-containing hydrocarbon mixtures and isomerization/further reaction to saturated $C_4$-dinitriles, preferably adiponitrile, in the presence of at least one catalyst according to the invention. When hydrocarbon mixtures are used for preparing monoolefinic $C_5$-mononitriles by the process according to the invention it is preferred to employ a hydrocarbon mixture which has a 1,3-butadiene content of least 10% by volume, preferably at least 25% by volume, in particular at least 40% by volume.

To prepare mixtures of monoolefinic $C_5$-mononitriles which contain, for example, 3-pentenenitrile and 2-methyl-3-butenonitrile and which are suitable as intermediates for further processing to adiponitrile, it is possible to employ pure butadiene or 1,3-butadiene-containing hydrocarbon mixtures.

1,3-Butadiene-containing hydrocarbon mixtures are obtainable on the industrial scale. Thus, for example, the processing of petroleum by steam cracking of naphtha results in a hydrocarbon mixture which is referred to as the $C_4$ cut and has a high total olefin content, about 40% being 1,3-butadiene and the remainder being monoolefins and polyunsaturated hydrocarbons plus alkanes. These streams always also contain small amounts, generally up to 5%, of alkynes, 1,2-dienes and vinylacetylene.

Pure 1,3-butadiene can be isolated from industrially obtainable hydrocarbon mixtures for example by extractive distillation.

The catalysts according to the invention can be employed advantageously for the hydrocyanation of such olefin-containing, in particular 1,3-butadiene-containing, hydrocarbon mixtures, ordinarily even without previous purification of the hydrocarbon mixture by distillation. Olefins which are possibly present and adversely affect the efficiency of the catalysts, such as alkynes or cumulenes, can be removed from the hydrocarbon mixture where appropriate before the hydrocyanation by selective hydrogenation. Suitable processes of selective hydrogenation are known to the skilled worker.

The hydrocyanation according to the invention can be carried out continuously, semicontinuously or batchwise. In a suitable variant of the process according to the invention, the hydrocyanation is carried out continuously. Suitable reactors for continuous reaction are known to the skilled worker and are described, for example, in Ullmanns Enzyklopädie der technischen Chemie, Volume 1, 3rd edition, 1951, pp. 743 et seq. A cascade of stirred vessels or a tubular reactor is preferably used for the continuous variant of the process according to the invention. Suitable, where appropriate pressure-resistant, reactors for the semicontinuous or continuous procedure are known to the skilled worker and are described, for example, in Ullmanns Enzyklopädie der technischen Chemie, Volume 1, 3rd edition, 1951, pp. 769 et seq. An autoclave, which can be provided if required with a stirrer and be lined, is generally used for the process according to the invention.

The hydrocyanation catalysts according to the invention can be removed from the discharge from the hydrocyanation reaction by conventional processes known to the skilled worker and can generally be employed anew for the hydrocyanation.

The invention is illustrated in detail by means of the following, nonlimiting examples.

EXAMPLES

Low-pressure Hydroformylation of 1-octene

Example 1

2.6 mg of rhodium biscarbonylacetylacetonate (0.01 mmol), 80 mg of ligand I.a according to the invention ($R^9$, $R^{10}=CF_3$, 0.20 mmol), 4.5 g of 1-octene (40 mmol) and 5 ml of Texanol® were reacted in a 50 ml glass autoclave with a $CO/H_2$ (1:1) synthesis gas mixture at $100°$ C. under 10 bar. After a reaction time of 4 hours, the autoclave was decompressed and emptied. The mixture was analyzed by GC with internal standard. The conversion amounted to 99%. The yield of nonanal isomers was 90%, and the selectivity for nonanal isomers was 90% (90.8% n-nonanal, 9.1% methyloctanal, 0.1% ethylheptanal).

Comparative Example 1

2.6 mg of rhodium biscarbonylacetylacetonate (0.01 mmol), 262 mg of triphenylphosphine (1.0 mmol), 10.0 g of 1-octene (90 mmol) and 10 ml of Texanol® were reacted in a 50 ml glass autoclave with a CO/H$_2$ (1:1) synthesis gas mixture at 100° C. under 10 bar. After a reaction time of 4 hours, the autoclave was decompressed and emptied. The mixture was analyzed by GC with internal standard. The conversion amounted to 100%. The yield of nonanal isomers was 88%, and the selectivity for nonanal isomers was 89% (73% n-nonanal, 25% 2-methyloctanal, 2% ethylheptanal).

We claim:

1. A catalyst comprising at least one complex of a metal of group VIII with at least one uni-, bi- or multidentate phosphinite ligand of the formula I

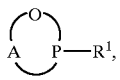  (I)

in which

A is a 2,2'-biphenylylene or 2,2'-binaphthylylene radical, which may have 1, 2 or 3 substituents selected from alkyl, alkoxy or halogen, R$^1$ is alkyl, aryl or hetaryl, each of which optionally has one, two or three substituents selected from alkyl, cycloalkyl, aryl, alkoxy, cycloalkyloxy, aryloxy, halogen, trifluoromethyl, nitro, cyano, carboxyl, carboxylate, acyl, sulfonyl, NE$^1$E$^2$ and alkylene-NE$^1$E$^2$, where E$^1$ and E$^2$ are identical or different and are selected from alkyl, cycloalkyl and aryl; or is a radical of the formula II

  (II)

in which

X is either C$_2$–C$_8$-alkylene bridge which is optionally interrupted by SiR$^a$R$^b$, N, NR$^c$, O or S, in which R$^a$ and R$^b$ are hydrogen, alkyl, alkoxy, halogen, trifluoromethyl, nitro or cyano, and R$^c$ is hydrogen, alkyl or aryl, where aryl is optionally mono- or disubstituted by alkyl, alkoxy, halogen, trifluoromethyl, nitro or cyano, optionally has one, two or three double bonds and/or is optionally fused once, twice or three times to aryl and/or hetaryl, where the aryl or hetaryl groups have, independently of one another, optionally one, two, three or four substituents selected from alkyl, cycloalkyl, aryl, alkoxy, cycloalkyloxy, aryloxy, halogen, trifluoromethyl, nitro, cyano, acyl, carboxyl, carboxylate, NE$^1$E$^2$ and alkylene-NE$^1$E$^2$, where E$^1$ and E$^2$ have the meanings indicated previously, and adjacent fused rings are optionally connected by SiR$^a$R$^b$, N, NR$^c$, O or S or by a C$_1$–C$_6$-alkylene bridge which optionally additionally carries a group selected from SiR$^a$R$^b$, N, NR$^c$, O or S, in which R$^a$, R$^b$ and R$^c$ are as defined above; or an optionally substituted metallocene bridge; and Y is a radical of the formula III

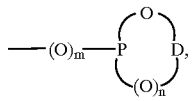  (III)

in which

D has the meanings indicated previously for A, and m and n are, independently of one another, 0 or 1, or a salt thereof.

2. A catalyst as defined in claim 1, in which X is a radical of the formula IV.1, IV.2, IV.3, IV.4, IV.5, IV.6, IV.7 or IV.8

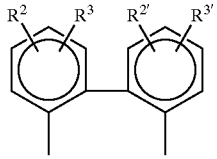  (IV.1)

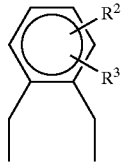  (IV.2)

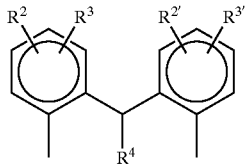  (IV.3)

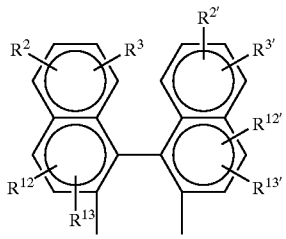  (IV.4)

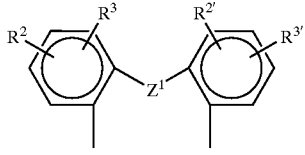  (IV.5)

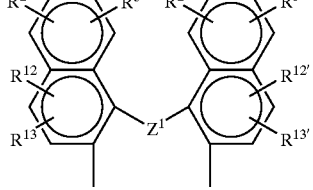  (IV.6)

-continued

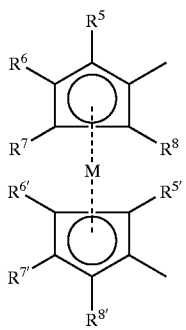
(IV.7)

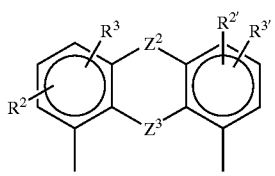
(IV.8)

in which

R², R²', R³ and R³' are, independently of one another, hydrogen, alkyl, alkoxy, halogen, trifluoromethyl, nitro, cyano, acyl, carboxyl or carboxylate, R⁴ is hydrogen, alkyl, or aryl, which may optionally be substituted by alkyl, alkoxy, halogen, trifluoromethyl, nitro or cyano, and R⁵, R⁵', R⁶, R⁶', R⁷, R⁷', R⁸, R⁸', R¹², R¹²', R¹³ and R¹³' have the meanings mentioned for R² and R³ or are, independently of one another, selected from cycloalkyl, aryl or alkyl, which may be interrupted by an oxygen atom or substituted by a radical of the formula NE¹E², where E¹ and E² have the meaning indicated above; or in each case two adjacent substituents R⁵, R⁶, R⁷, R⁸ and/or R⁵', R⁶', R⁷', R⁸' represent, with the part of the cyclopentadienyl ring connecting them, an aromatic or nonaromatic 5- to 7-membered carbocycle or heterocycle, where the heterocycle has 1, 2 or 3 heterogroups selected from O, N, NR$^c$ and S, M is Fe, Co, Ni, Ru, Os, Rh, Mn, Cr or V, Z¹ is O, S and NR$^c$ or a C₂- to C₃-alkylene bridge which is interrupted by O, S or NR$^c$, Z² and Z³ are, independently of one another, CH₂, SiR$^a$R$^b$, O, S, NR$^c$ or CR$^a$R$^b$, where R$^a$, R$^b$ and R$^c$ each have the meaning indicated above.

3. A catalyst as defined in either of the preceding claims, where the phosphinite ligand of the formula I is selected from ligands of the formulae Ia to Ii

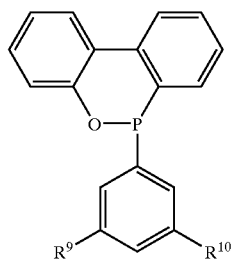
(Ia)

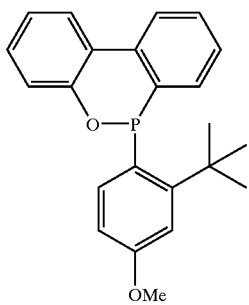
(Ib)

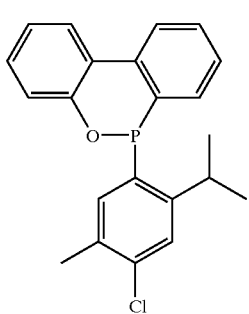
(Ic)

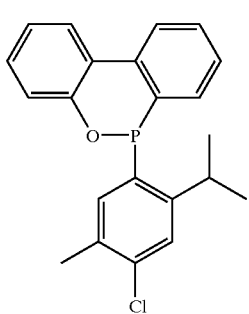
(Id)

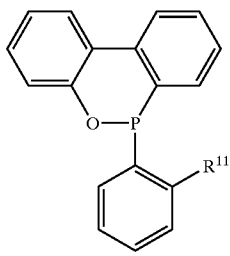
(Ie)

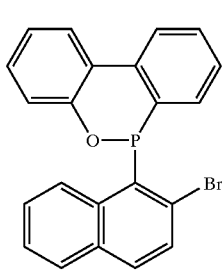
(If)

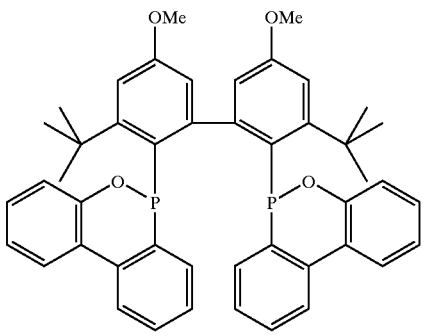

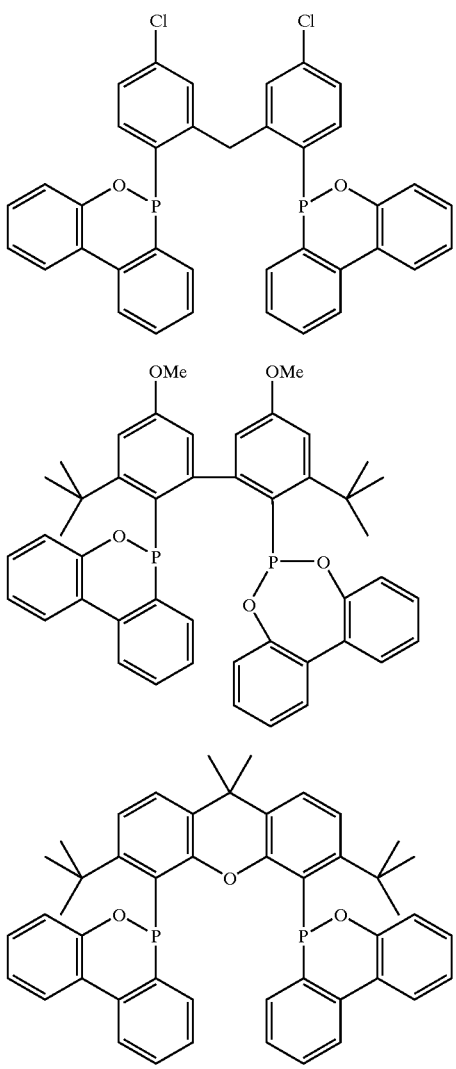

in which

R[9] and R[10] are, independently of one another, hydrogen or trifluoromethyl, and R[11] is fluorine or trifluoromethyl.

4. A catalyst as defined in claim 1, wherein the metal of group VIII is selected from cobalt, nickel, ruthenium, rhodium, palladium and platinum.

5. A catalyst as defined in claim 1, which additionally comprises at least one other ligand different from ligands of the formula I and selected from halides, amines, carboxylates, acetylacetonate, aryl- or alkylsulfonates, hydrides, CO, olefins, dienes, cycloolefins, nitrites, N-containing heterocycles, aromatic and heteroaromatic compounds, ethers, $PF_3$, and uni-, bi- and multidentate phosphine, phosphinite, phosphonite and phosphite ligands.

6. A process for the hydroformylation of compounds which contain at least one ethylenic double bond, by reaction with carbon monoxide and hydrogen in the presence of a hydroformylation catalyst, wherein a catalyst as defined in claim 1 is employed as hydroformylation catalyst.

7. A process as defined in claim 6, employing for the hydroformylation a compound which contains at least one terminal double bond, wherein a mixture of isomeric aldehydes with an n/iso ratio of at least 3:1, in particular 5:1, particularly preferably 8:1, is obtained.

8. A process for the hydrocyanation of compounds which contain at least one ethylenic double bond, by reaction with hydrogen cyanide in the presence of a hydrocyanation catalyst, wherein a catalyst as defined in claim 1 is employed as hydrocyanation catalyst.

9. A process as defined in claim 6, wherein the hydroformylation catalyst or the hydrocyanation catalyst is prepared in situ with at least one phosphinite ligand of the general formula I, a compound or a complex of a metal of group VIII and, where appropriate, an activator being reacted in an inert solvent under the hydroformylation or hydrocyanation conditions.

10. The process of claim 7, wherein a mixture of isomeric aldehydes with an n/iso ratio of at least 8:1 is obtained.

* * * * *

UNITED STATES PATENT AND TRADEMARK OFFICE
CERTIFICATE OF CORRECTION

PATENT NO.    : 6,486,359 B1
DATED         : November 26, 2002
INVENTOR(S)   : Maas et al.

It is certified that error appears in the above-identified patent and that said Letters Patent is hereby corrected as shown below:

Column 22,
Line 13, "nitrites" should be -- nitriles --.

Signed and Sealed this

Ninth Day of September, 2003

JAMES E. ROGAN
*Director of the United States Patent and Trademark Office*